(12) United States Patent  
McMichael et al.

(10) Patent No.: US 7,867,253 B2
(45) Date of Patent: Jan. 11, 2011

(54) SUTURE RETENTION HUB

(75) Inventors: Donald Jay McMichael, Roswell, GA (US); John Anthony Rotella, Roswell, GA (US); Nathan Christopher Griffith, Roswell, GA (US); Thomas Gregory Estes, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 635 days.

(21) Appl. No.: 11/848,495

(22) Filed: Aug. 31, 2007

(65) Prior Publication Data

US 2009/0062853 A1  Mar. 5, 2009

(51) Int. Cl.
*A61B 17/04* (2006.01)
(52) U.S. Cl. ....................................................... 606/232
(58) Field of Classification Search ......... 606/144–146, 606/148, 232; 242/153; 24/712.6, 713.6, 24/132 AA, 132 R, 132 WL, 115 R
See application file for complete search history.

(56) References Cited

U.S. PATENT DOCUMENTS

| | | | |
|---|---|---|---|
| 2,075,508 A | 3/1937 | Davidson | |
| 3,664,345 A | 5/1972 | Dabbs et al. | |
| 3,976,079 A | 8/1976 | Samuels et al. | |
| 4,249,535 A | 2/1981 | Hargest, III | |
| 4,291,698 A | 9/1981 | Fuchs et al. | |
| 4,315,513 A | 2/1982 | Nawash et al. | |
| 4,393,873 A | 7/1983 | Nawash et al. | |
| 4,666,433 A | 5/1987 | Parks | |
| 4,685,901 A | 8/1987 | Parks | |
| 4,701,163 A | 10/1987 | Parks | |
| 4,705,040 A | 11/1987 | Mueller et al. | |
| 4,750,492 A | 6/1988 | Jacobs | |
| 4,798,592 A | 1/1989 | Parks | |
| 4,823,794 A | 4/1989 | Pierce | |
| 4,852,568 A | 8/1989 | Kensey | |
| 4,890,612 A | 1/1990 | Kensey | |
| 5,019,093 A | 5/1991 | Kaplan et al. | |
| 5,037,429 A | 8/1991 | Hermes et al. | |

(Continued)

FOREIGN PATENT DOCUMENTS

EP  1159919 A2  12/2001

(Continued)

OTHER PUBLICATIONS

English Abstract for EP 1159919, Dec. 5, 2001, Derwent WPI.

*Primary Examiner*—Gary Jackson
*Assistant Examiner*—Gregory Anderson
(74) *Attorney, Agent, or Firm*—Karl V. Sidor; Sue C. Watson

(57) ABSTRACT

A suture retention hub is provided. It includes a base configured to moveably hold a handle within at least a portion of the base. The base has an aperture which extends through the base. The hub also includes a handle configured to moveably fit into the portion of the base. The handle has an aperture formed therethough as well. When a suture is positioned in the apertures and the base and handle are positioned such that the apertures are substantially in an axial alignment, the suture moves readily through the apertures in the hub. Then the base and handle are positioned such that the apertures are not in a substantial axial alignment, the suture is frictionally crimped and it is prevented from moving through the hub.

19 Claims, 11 Drawing Sheets

U.S. PATENT DOCUMENTS

| | | | |
|---|---|---|---|
| 5,041,129 A | 8/1991 | Hayhurst et al. |
| 5,049,138 A | 9/1991 | Chevalier et al. |
| 5,051,272 A | 9/1991 | Hermes et al. |
| 5,053,047 A | 10/1991 | Yoon |
| 5,061,274 A | 10/1991 | Kensey |
| 5,074,846 A | 12/1991 | Clegg et al. |
| 5,112,310 A | 5/1992 | Grobe |
| 5,121,836 A | 6/1992 | Brown et al. |
| 5,123,912 A | 6/1992 | Kaplan et al. |
| 5,123,914 A | 6/1992 | Cope |
| 5,129,511 A | 7/1992 | Brown et al. |
| RE34,021 E | 8/1992 | Mueller et al. |
| 5,154,283 A | 10/1992 | Brown |
| 5,167,627 A | 12/1992 | Clegg et al. |
| 5,192,302 A | 3/1993 | Kensey et al. |
| 5,222,976 A | 6/1993 | Yoon |
| 5,222,978 A | 6/1993 | Kaplan et al. |
| 5,226,912 A | 7/1993 | Kaplan et al. |
| 5,246,104 A | 9/1993 | Brown et al. |
| 5,258,015 A | 11/1993 | Li et al. |
| 5,261,210 A | 11/1993 | Brown |
| 5,261,886 A | 11/1993 | Chesterfield et al. |
| 5,269,809 A | 12/1993 | Hayhurst et al. |
| 5,273,529 A | 12/1993 | Idowu |
| 5,306,289 A | 4/1994 | Kaplan et al. |
| 5,307,924 A | 5/1994 | Manosalva et al. |
| 5,312,435 A | 5/1994 | Nash et al. |
| 5,318,543 A | 6/1994 | Ross et al. |
| 5,330,503 A | 7/1994 | Yoon |
| 5,341,823 A | 8/1994 | Manosalva et al. |
| 5,359,831 A | 11/1994 | Brown et al. |
| 5,366,081 A | 11/1994 | Kaplan et al. |
| RE34,866 E | 2/1995 | Kensey et al. |
| 5,391,159 A | 2/1995 | Hirsch et al. |
| 5,417,036 A | 5/1995 | Brown |
| 5,425,445 A | 6/1995 | Brown et al. |
| 5,447,966 A | 9/1995 | Hermes et al. |
| 5,451,212 A | 9/1995 | Andersen |
| 5,456,697 A | 10/1995 | Chesterfield et al. |
| 5,462,162 A | 10/1995 | Kaplan et al. |
| 5,468,252 A | 11/1995 | Kaplan et al. |
| 5,531,699 A | 7/1996 | Tomba et al. |
| 5,531,759 A | 7/1996 | Kensey et al. |
| 5,531,761 A | 7/1996 | Yoon |
| 5,545,178 A | 8/1996 | Kensey et al. |
| 5,626,614 A | 5/1997 | Hart |
| 5,702,352 A | 12/1997 | Kimura et al. |
| 5,851,195 A | 12/1998 | Gill |
| 6,030,364 A | 2/2000 | Durgin et al. |
| 6,039,714 A | 3/2000 | Cracauer et al. |
| 6,063,106 A | 5/2000 | Gibson |
| 6,077,250 A | 6/2000 | Snow et al. |
| 6,090,073 A | 7/2000 | Gill |
| 6,110,183 A | 8/2000 | Cope |
| 6,186,985 B1 | 2/2001 | Snow |
| 6,260,699 B1 | 7/2001 | Kaplan et al. |
| 6,293,961 B2 | 9/2001 | Schwartz et al. |
| 6,315,789 B1 | 11/2001 | Cragg |
| 6,319,271 B1 | 11/2001 | Schwartz et al. |
| 6,328,720 B1 | 12/2001 | McNally et al. |
| 6,332,877 B1 | 12/2001 | Michels |
| 6,402,722 B1 | 6/2002 | Snow et al. |
| 6,432,123 B2 | 8/2002 | Schwartz et al. |
| 6,582,443 B2 | 6/2003 | Cabak et al. |
| 6,626,919 B1 | 9/2003 | Swanstrom |
| 6,669,707 B1 | 12/2003 | Swanstrom et al. |
| 6,673,058 B2 | 1/2004 | Snow |
| 6,699,263 B2 | 3/2004 | Cope |
| 6,773,440 B2 | 8/2004 | Gannoe et al. |
| 6,896,665 B2 | 5/2005 | Picha et al. |
| 6,902,541 B2 | 6/2005 | McNally et al. |
| 6,966,916 B2 | 11/2005 | Kumar |
| 6,997,931 B2 | 2/2006 | Sauer et al. |
| 7,033,380 B2 | 4/2006 | Schwartz et al. |
| 7,066,944 B2 | 6/2006 | Laufer et al. |
| 2003/0229361 A1 | 12/2003 | Jackson |
| 2004/0034369 A1 | 2/2004 | Sauer et al. |
| 2004/0102809 A1 | 5/2004 | Anderson |
| 2004/0153103 A1 | 8/2004 | Schwartz et al. |
| 2005/0004540 A1 | 1/2005 | McNally et al. |
| 2005/0143691 A1 | 6/2005 | Picha et al. |
| 2005/0149120 A1 | 7/2005 | Collier et al. |
| 2005/0149121 A1 | 7/2005 | Crombie et al. |
| 2005/0165419 A1 | 7/2005 | Sauer et al. |
| 2005/0203550 A1 | 9/2005 | Laufer et al. |
| 2006/0095008 A1 | 5/2006 | Lampropoulos et al. |
| 2006/0100643 A1 | 5/2006 | Laufer et al. |
| 2006/0135996 A1 | 6/2006 | Schwartz et al. |
| 2006/0184200 A1 | 8/2006 | Jervis |

FOREIGN PATENT DOCUMENTS

| | | |
|---|---|---|
| EP | 1749481 A1 | 2/2007 |
| WO | WO 95/03837 | 2/1995 |
| WO | WO 02/066108 | 8/2002 |
| WO | WO 2006/111394 | 10/2006 |

SUTURE RETENTION HUB

BACKGROUND OF THE INVENTION

This invention relates to an external hub used in conjunction with a suture and, in some applications, an internal anchor, for establishing stomas, drains, and so forth, in intra-abdominal viscera, blood vessels, and the like.

The insertion of feeding tubes and drain tubes often require the use of an internal anchor "T-bar" fastener or other fastener which is attached to a tension filament or suture. The fastener is positioned in a blood vessel or organ via a needle, and the opposite end of the suture extends to the outer surface of a patient's skin. In some procedures, this external opposite end of the suture is temporarily stitched to the outer surface of the patient's skin. In other procedures, the external opposite end of the suture is clamped via an external retention device that usually includes a cotton ball, a plastic washer, plastic tubing, and one or more metal crimps. There are problems with both of these external suture retention methods.

Patients dislike having external stitches, which can pull against the skin, or catch on clothing or gowns. Further, additional suturing requires additional skill and safety risks for the physician. Moreover, after external sutures are in place, there may be confusion as to why the sutures are present. There is a risk that a health care provider, as a result of this confusion, will try to cut and pull out the external suture(s). Issues also exist with retention devices.

One retention device, described above, has many drawbacks. It cannot easily be cleaned. That is, the cotton ball, which is positioned against the patient's skin, may easily harbor bacteria and microorganisms, and may be difficult to change. Further, the device uses plastic tubing, washers, and metal crimps. The combination of components in this retention device results in a high profile away from the skin, typically 0.75 inches or more. These devices may pull, catch on clothing, or rub against the skin, causing abrasion or necrosis due to pressure.

There exists a need for a suture retention hub that has a low profile against a patient's skin. Such a device would be easily recognizable to health care workers as a retention hub for anchoring an internally disposed device via a suture. The hub would desirably by formed at least partially from a material which has excellent biocompatibility and ease of cleaning. Such a material would desirably be soft and provide cushioning against a patient's skin, to prevent abrasion and/or necrosis. Such a hub would permit an adequate retention force, and desirably would permit easy application of tension on the suture by a simple manipulation of the hub.

DEFINITIONS

As used herein, the terms "comprise", "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "has" and/or "have", and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

As used herein, the terms "resilient", "resilience" and/or "resiliency" and any derivatives thereof refers to the physical property of an object and/or a material that can return to its original form, shape and/or position after deformation such as being bent, compressed, or stretched that does not exceed its elastic limit.

As used herein, the term "couple" includes, but is not limited to, joining, connecting, fastening, linking, or associating two things integrally or interstitially together.

As used herein, the term "configure" or "configuration", and derivatives thereof means to design, arrange, set up, or shape with a view to specific applications or uses. For example: a military vehicle that was configured for rough terrain; configured the computer by setting the system's parameters.

As used herein, the term "substantially" refers to something which is done to a great extent or degree; a significant or great amount; for example, as used herein "substantially" as applied to "substantially" covered means that a thing is at least 70 percent covered.

As used herein, the term "alignment" refers to the spatial property possessed by an arrangement or position of things in a straight line or in parallel lines.

As used herein, the terms "orientation" or "position" used interchangeably herein refer to the spatial property of a place where or way in which something is situated; for example, "the position of the hands on the clock."

As used herein, the term "about" refers to an amount that is plus or minus 10 percent of a stated number or a stated or implied range.

These terms may be defined with additional language in the remaining portions of the specification.

SUMMARY OF THE INVENTION

In response to the difficulties and problems discussed herein, a suture retention hub is provided. It includes a base configured to moveably hold a handle within at least a portion of the base. The base is formed to include an aperture therethrough. The hub also includes a handle configured to moveably fit within a portion of the base, a portion of the handle has an aperture formed therethrough, the portion positioned within the portion of the base to permit movement of the handle. The aperture in the base and the aperture in the handle are substantially in an axial alignment when the handle is positioned transversely relative to an upper surface of the base. In this position, a suture positioned in the apertures moves readily through the apertures. The aperture in the base and the aperture in the handle are substantially out of an axial alignment when an upper surface of the handle is positioned in a parallel alignment relative to the upper surface of the base. In this position, a suture positioned in the apertures is frictionally crimped in its position in the handle and the base, respectively, thereby preventing movement of the suture within the hub.

In another aspect of the invention, a suture retention hub is provided. The suture retention hub includes a first base including an upper surface. The hub also includes a second base configured to couple to the first base. At least one of the first base and the second base is formed to include at least one aperture therethough. When the second base is positioned substantially at a 90 degree angle relative to the upper surface of the first base, a suture positioned through the aperture is moveable through the hub. When the second base is positioned substantially parallel to the upper surface of the first base, a suture positioned through the aperture is not moveable through the hub.

In yet another aspect of the invention, a suture retention hub is provided. The suture retention hub includes a first base. The hub also includes a second base coupled to the first base. At least one of the first base and the second base has an opening configured to hold a suture. A suture positioned in the opening is moveable relative to both the first base and the second base when the hub is positioned in an un-locked position. A suture positioned in the opening is non-moveable relative to both the first base and the second base when the hub is positioned in a locked position.

Additional features and advantages of the present invention will be revealed in the following detailed description. Both the foregoing summary and the following detailed description and examples are merely representative of the invention, and are intended to provide an overview for understanding the invention as claimed.

DETAILED DESCRIPTION

Figure 1:
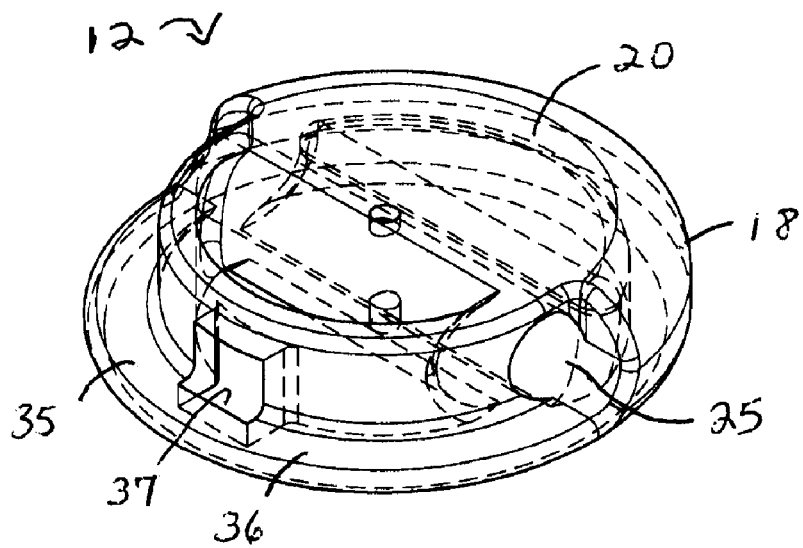
FIG. 1 is a perspective view of a top of a base or first base of a suture retention hub of the present invention.
Figure 2:
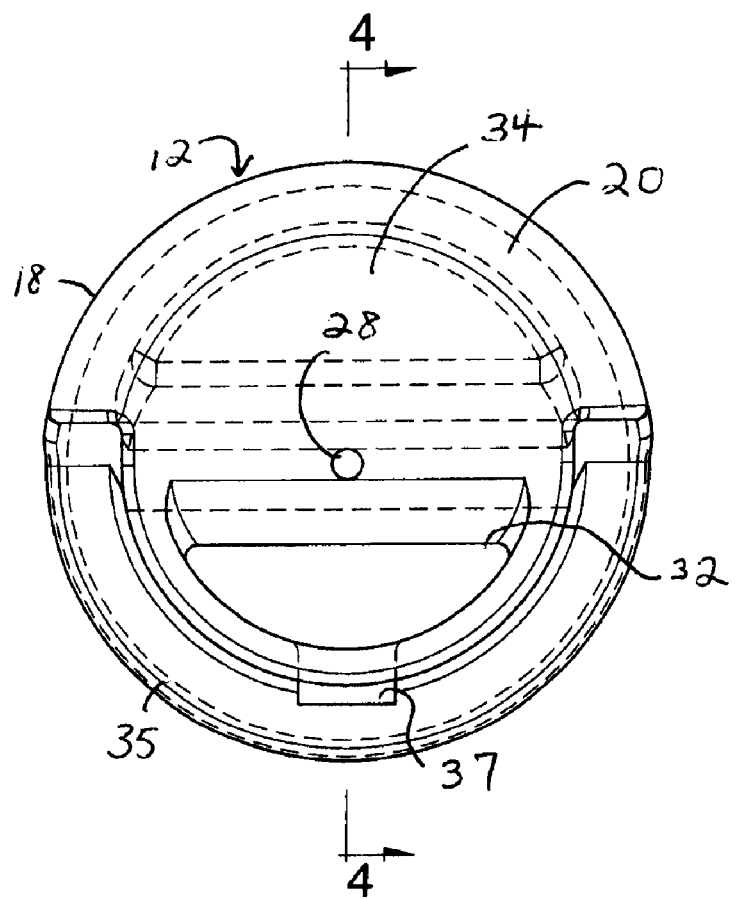
FIG. 2 is a top plan view of the base or first base of FIG. 1.
Figure 3:
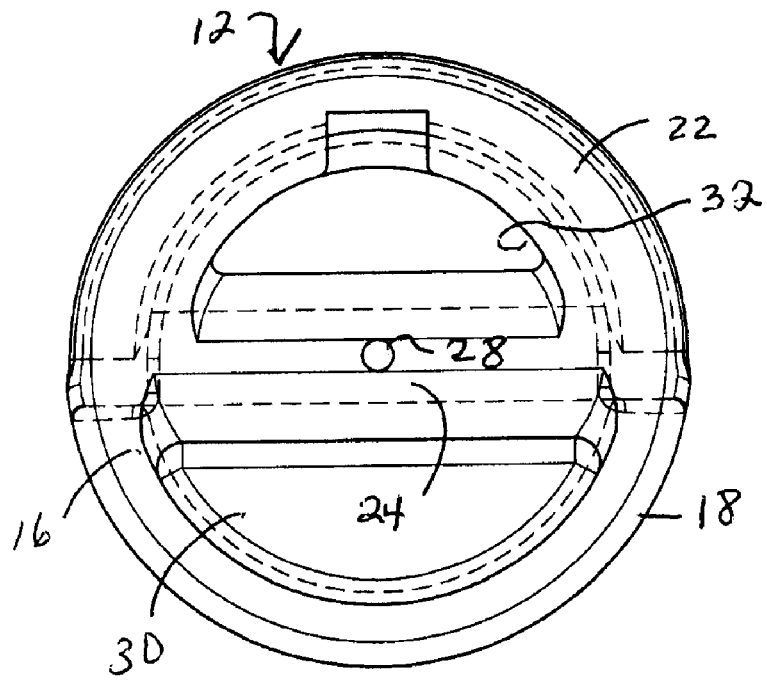
FIG. 3 is a bottom plan view of the base or first base of FIG. 1.
Figure 4:
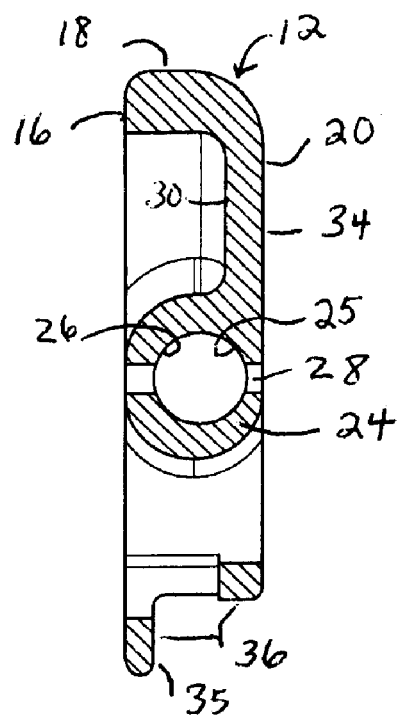
FIG. 4 is a sectional view of FIG. 2 taken along lines 4-4.
Figure 5:
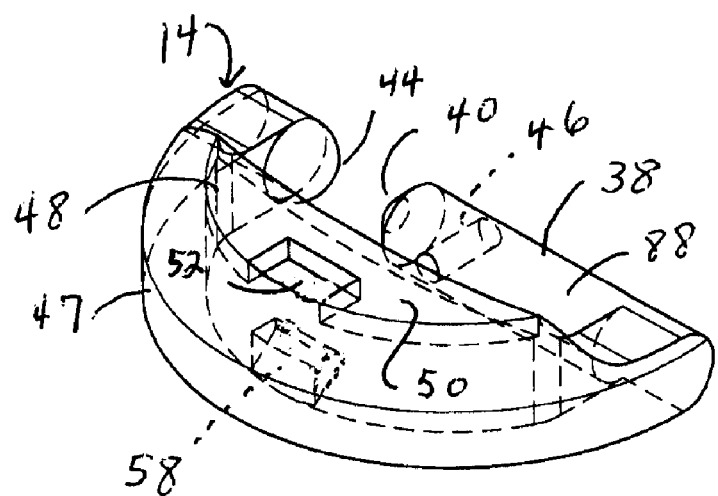
FIG. 5 is a perspective view of a top of a handle or second base of a suture retention hub of the present invention.
Figure 6:
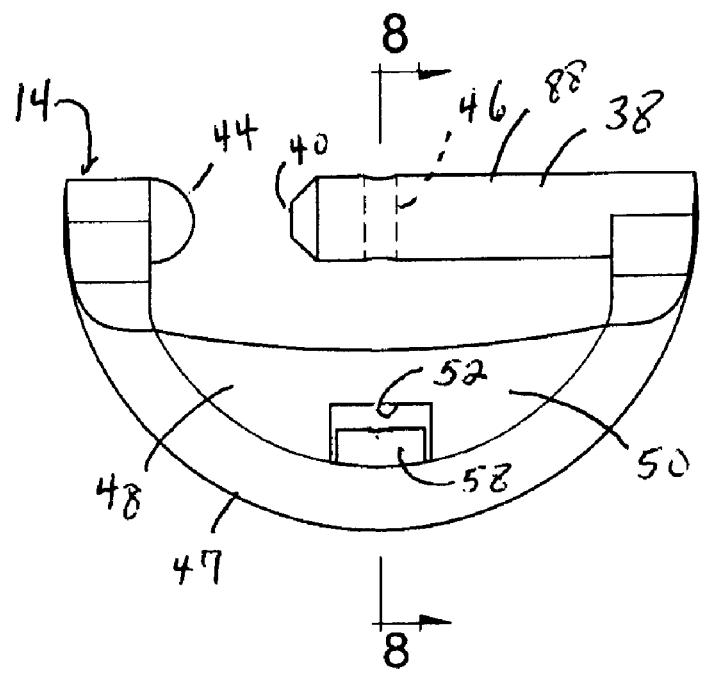
FIG. 6 is a top plan view of the handle or second base of FIG. 5.
Figure 7:
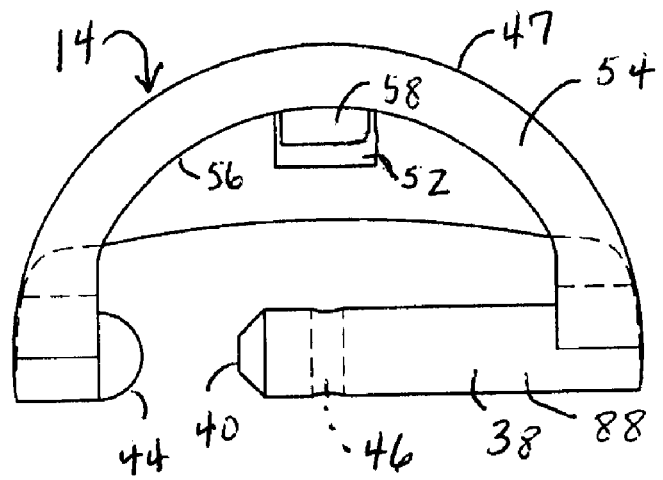
FIG. 7 is a bottom plan view of the handle or second base of FIG. 5.
Figure 8:
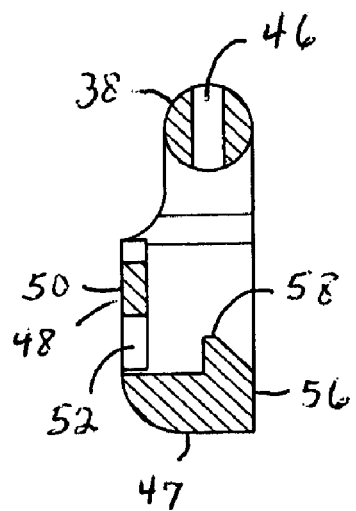
FIG. 8 is a sectional view of FIG. 6 taken along lines 8-8.
Figure 9:
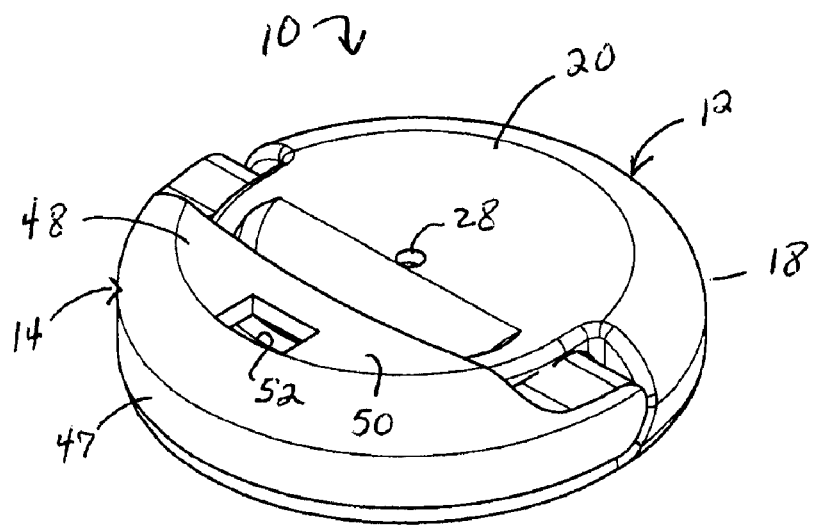
FIG. 9 is a perspective view of a top of the suture retention hub of the present invention, showing both the base or first base and the handle or second base.
Figure 10:
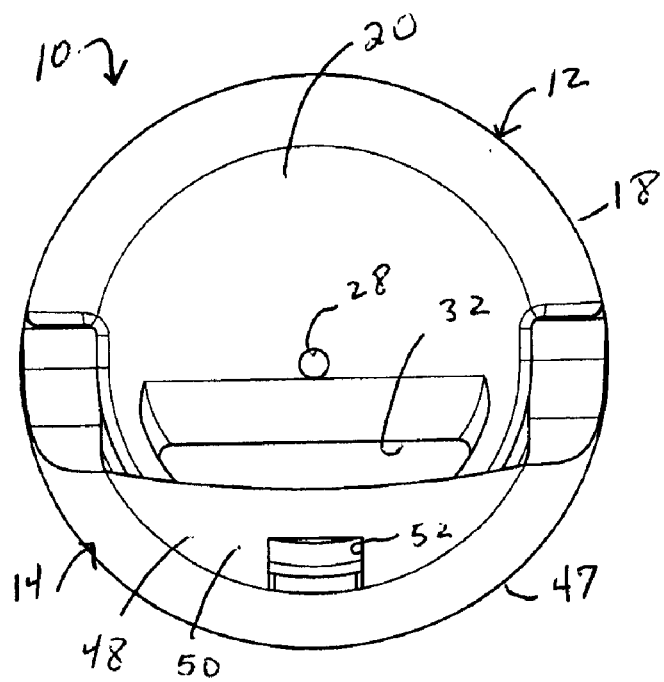
FIG. 10 is a top plan view of the suture retention hub of FIG. 9.
Figure 11:
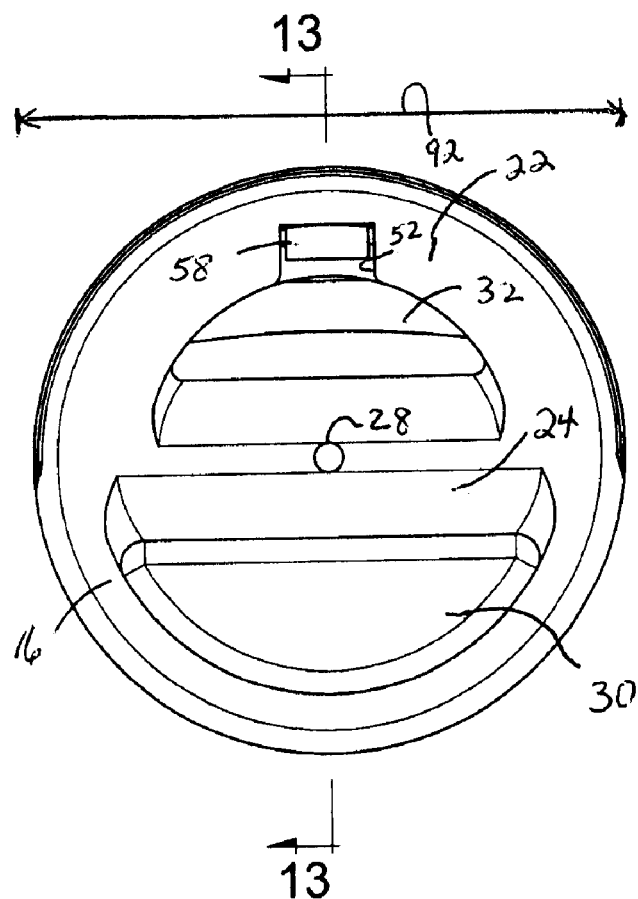
FIG. 11 is a bottom plan view of the suture retention hub of FIG. 9.
Figure 12:
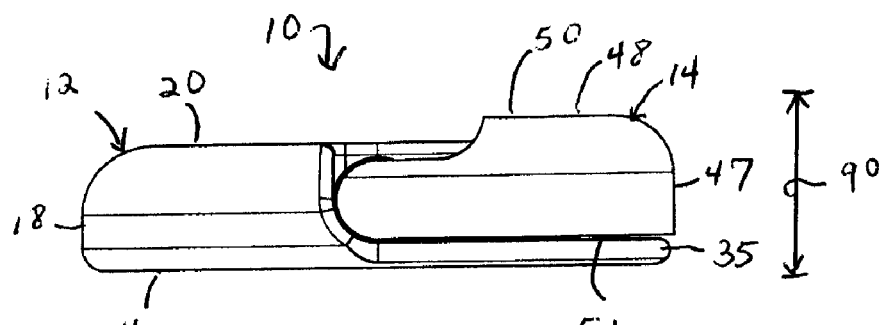
FIG. 12 is an elevated side view of the suture retention hub of FIG. 9.

Reference will now be made in detail to one or more embodiments of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The present invention relates to a suture retention hub. The hub desirably is used to hold a filament or suture in tension on an external portion of a patient's skin, and may be used to provide tension to an internally disposed device via a suture. Such a device may include, for example, but not by way of limitation, a "T-bar" fastener or other device which is positioned internally, usually in an organ or blood vessel. Referring now to FIGS. 1-22 in general, and 1-16 in particular, a suture retention hub 10 is illustrated. The hub 10 includes a first base or base 12 and a movable, pivotal second base or handle 14. The first base or base 12, as shown in FIG. 1-4, includes a lower surface 16 (FIG. 3) having a substantially circular outer perimeter 18, and an upper surface 20.

A portion 22 (FIG. 3) of the perimeter 18 of the first base or base 12 adjacent the lower surface 16 is constructed to have a flat wheel or disk-like appearance. A bar 24 is provided and extends across the lower surface 16 from perimeter 18 to perimeter 18 of the first base or base 12. The bar 24 has an opening 25 which extends therethrough which defines an inner surface 26. The bar 24 also has an aperture 28 formed transversely therethrough. On one side of the bar 24, an indentation 30 is provided between the bar 24 and the perimeter 18 of the first base or base 12 on the lower surface 16. On the opposite side of the bar 24, an opening 32 extends between the bar 24 and the perimeter 18. The opening 32 extends from the lower surface 16 through the upper surface 20 of the first base or base 12.

An outer portion of the upper surface 20 of the first base or base 12 generally has a circular perimeter and the upper surface 20 includes a semi-circular raised flat surface 34. The opening 28 through the first base or base 12 is generally, for example, is desirably generally semi-circular in configuration, being defined between a portion of the perimeter 18 and the bar 24. An edge 35 of the perimeter 18 is adjacent the opening 28, and provides an L-shaped flange 36 along a portion of the perimeter 18 on the upper surface 20. The L-shaped flange includes an opening 37 therein.

The pivotal second base or handle 14, as illustrated in FIGS. 5-8, couples to the first base or base 12 via a pivot pin 38. The pivotal second base or handle 14 is also of a generally semi-circular configuration, and includes a pivot pin 38 having a boss 40 at a free end thereof. The pivot pin 38 and boss 44 are in an axial alignment with an opposing, spaced-apart boss 44 formed on a portion of the second base or handle 14. The pivot pin 38 has an aperture 46 formed therethrough. The aperture 46 may be generally in an axial alignment with the aperture 28 positioned transversely through the bar 24 of the first base or base 12 when the second base or handle 14 is pivoted into a transverse position relative to the upper surface 20 of the first base or base 12.

Figure 13:
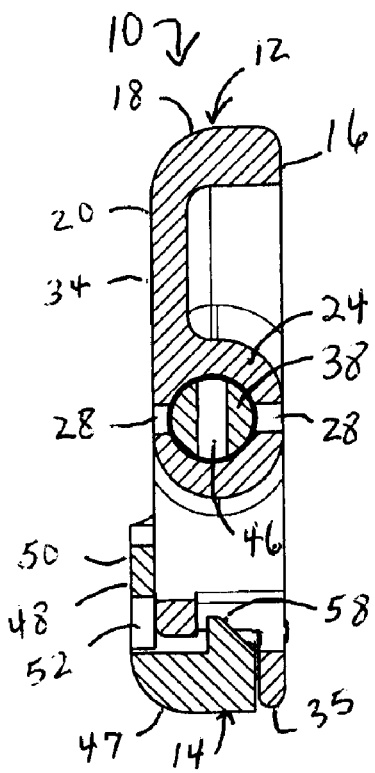
FIG. 13 is a sectional view of FIG. 11 taken along lines 13-13, showing the apertures.
Figure 14:
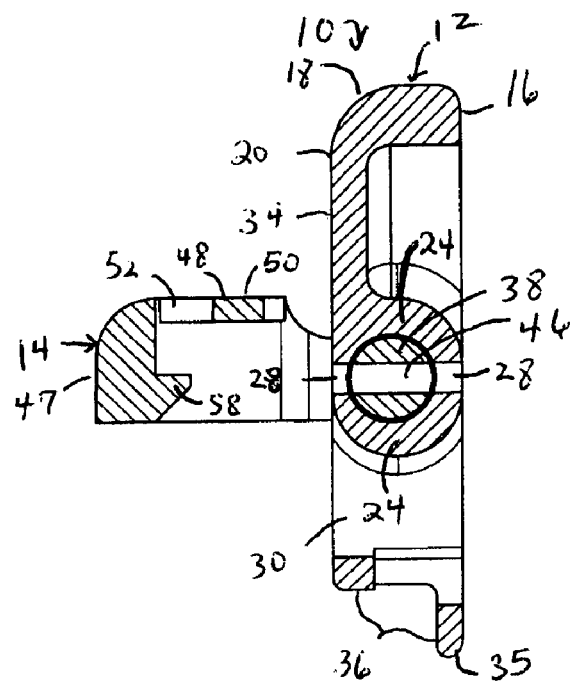
FIG. 14 is a sectional view similar to FIG. 13, but showing the position of the apertures with the handle or second base positioned transversely relative to the base or first base, showing the alignment of the apertures in the handle or second base and the base or first base.

The second base or handle 14 includes a perimeter 47 and an upper surface 48 which desirably includes a lip 50 formed to include a small opening 52 therein. On a lower surface 54 of the second base or handle 14, an inner edge 56 of the perimeter 47 includes a knob 58 positioned thereon. The second base or handle 14 is formed from a material which has some resiliency. Therefore, at least portions of the second base or handle 14 may resiliently bend to permit assembly with the first base or base 12. When assembled, the pivot pin 38 of the second base or handle 14 is positioned in the opening 25 of the bar 24 of the first base or base 12 (FIG. 13). The second base or handle 14 is moveable or pivotable with respect to the first base or base 12 when in an opened position (FIG. 14). The second base or handle 14 is frictionally held in a non-pivoting position when the second base or handle 14 is positioned against the flange 36 and the knob 58 is positioned through the opening 37 of the flange 36. The knob 58 and the opening 37 cooperate to provide a latch assembly for locking and un-locking the hub 10, thereby positioning and holding the second base or handle 14 in a locked position (FIG. 13) relative to the first base or base 12. In this position, the aperture 46 formed through the pivot pin 38 is moved out of its general axial alignment (which occurs when the second base or handle 14 is positioned transversely at a about a 90 degree angle relative to the upper surface 20 of the first base or base 12). That is, the aperture 46 positioned through the pivot pin 38, in the locked position, is positioned at about a 90 degree angle with respect to the aperture 28 in the bar 24 of the first base or base 12.

The hub 10 may include a soft outer cover 60, as illustrated in FIGS. 17-22. The cover 60 is desirably, but not by way of limitation, a one piece cover 60 that is soft and has some resiliency to allow it to stretch to fit over the hub 10. Such a soft outer cover may be constructed from, for example, but not by way of limitation, a medical grade thermoplastic polyurethane. This type of material is desirably used to disburse the pressure from tension on the hub 10 against a patient's skin, thereby reducing the possibility of the hub 10 causing irritation or the development of a pressure sore or necrosis occurring under the hub 10.

The cover 60 desirably is generally disk-shaped, with a lower outer surface 62, an outer perimeter 64 and an upper outer surface 66. The cover 60 may desirably include an opening 68 and a flap 70 formed adjacent the opening 68. The hub 10 is desirably positioned through the opening 68 and the lower surface 16 of the first base or base 12 of the hub 10 is positioned against an inner surface 72 and adjacent the lower surface 62 of the cover 60. The hub 10 is substantially encompassed by the cover 60. The hub 10 is positioned such that the second base or handle 14 is desirably positioned adjacent the opening 68 in the upper surface 66 of the cover 60. The cover 60 includes an aperture 74 positioned through the lower surface 62 and a slit 76 positioned through the flap 70 of the upper surface 66 of the cover 60. The aperture 74 and the end of the slit 76 of the cover 60 are desirably generally aligned with the aperture 28 positioned through the bar 24 of the first base or base 12.

Figure 15:
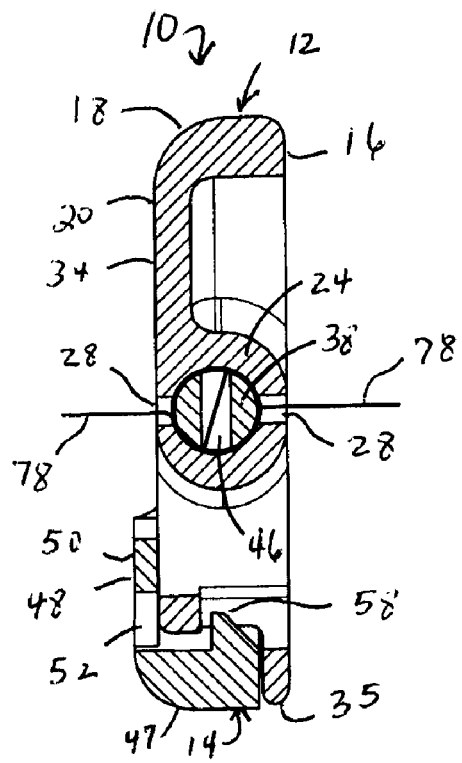
FIG. 15 is a sectional view similar to FIG. 13, but showing a suture positioned through the apertures in the base or first base and the handle or second base, showing the circuitous, crimped position of the aperture.
Figure 16:
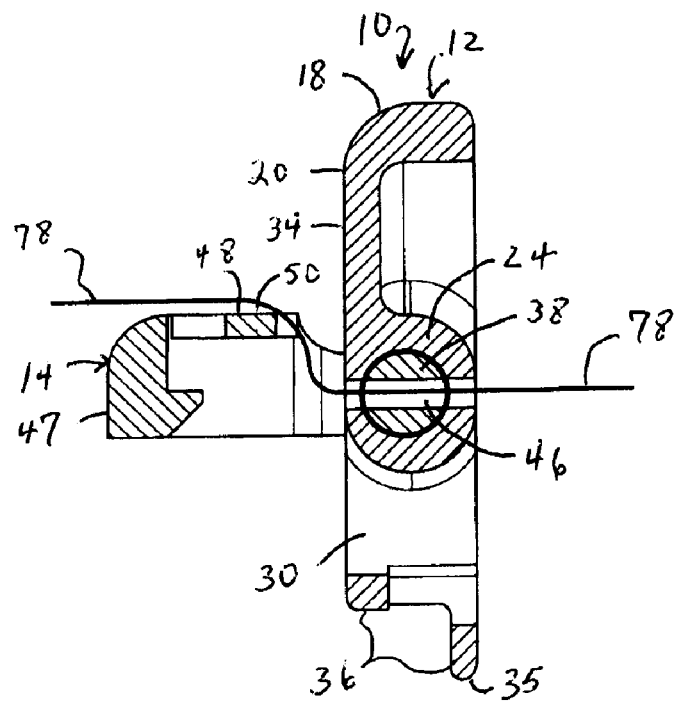
FIG. 16 is a sectional view similar to FIG. 14, but showing a suture positioned through the apertures in the base or first base and the handle or second base, showing the substantial axial alignment of the suture in the apertures.
Figure 17:
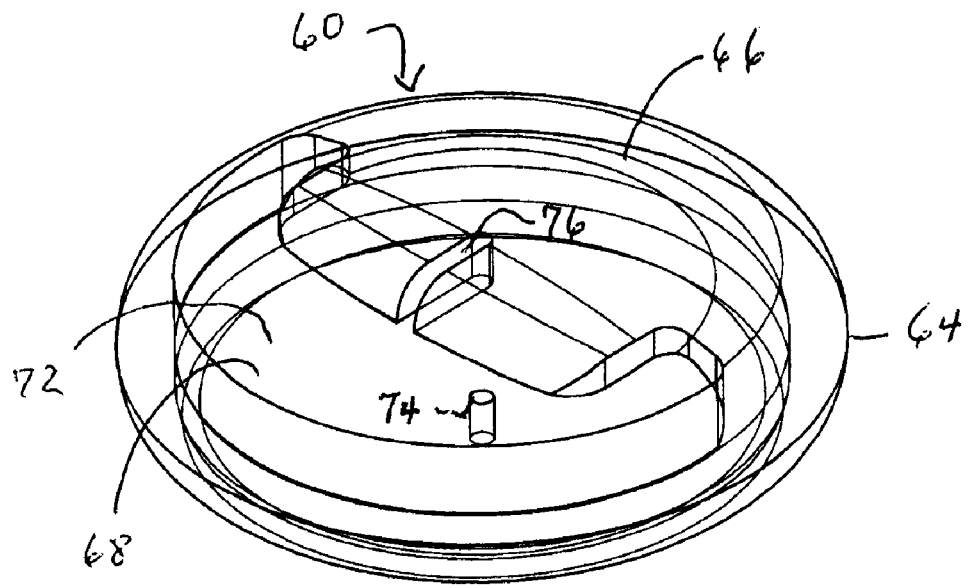
FIG. 17 is a perspective view of a top of a cover for the suture retention hub.
Figure 18:
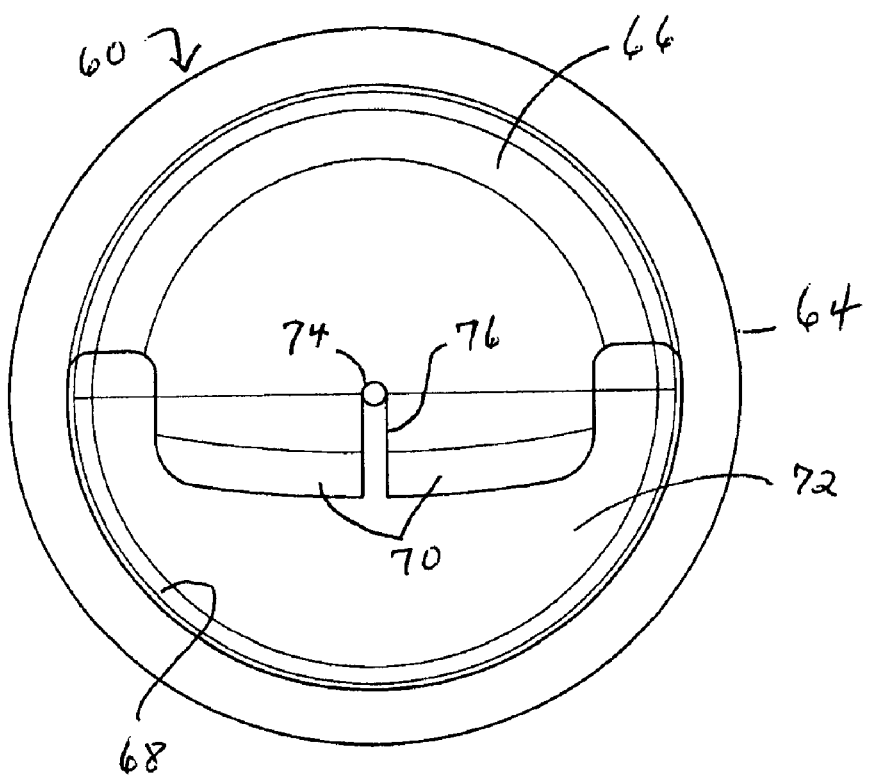
FIG. 18 is a top plan view of the cover of FIG. 17.
Figure 19:
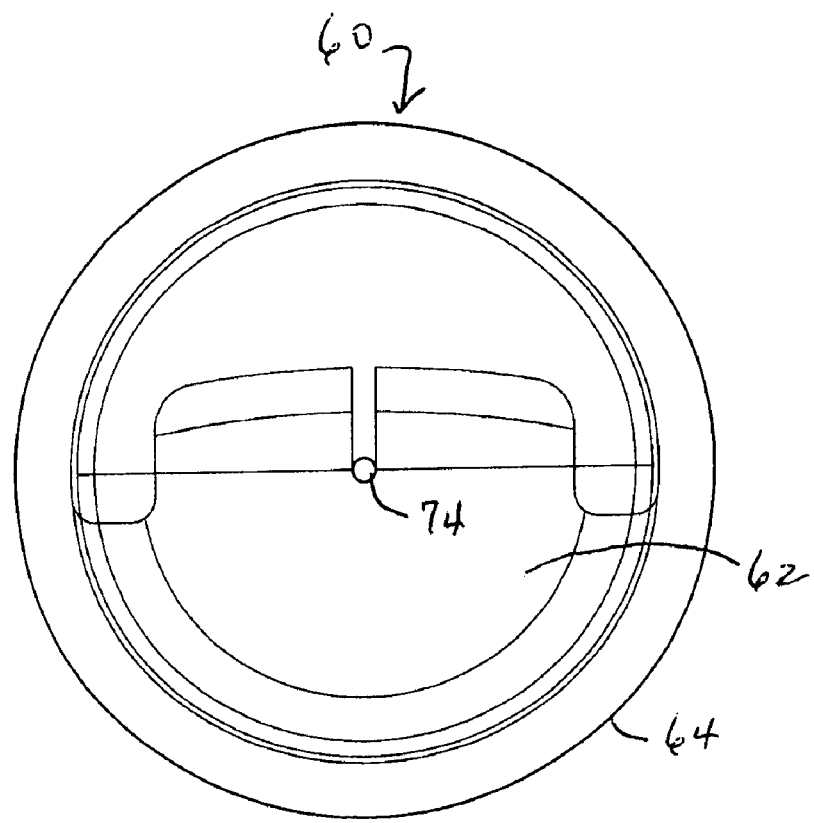
FIG. 19 is a bottom plan view of the cover of FIG. 17.
Figure 20:
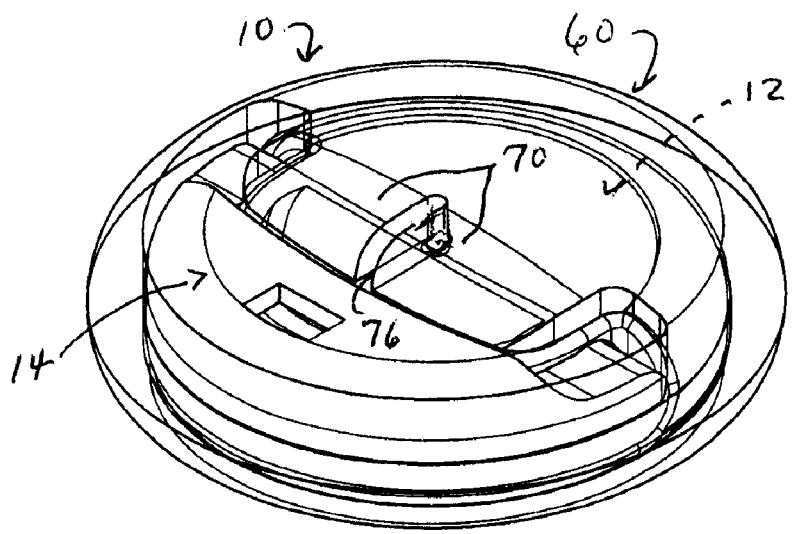
FIG. 20 is a perspective view of the cover of FIG. 17, but with a suture retention hub positioned therein.
Figure 21:
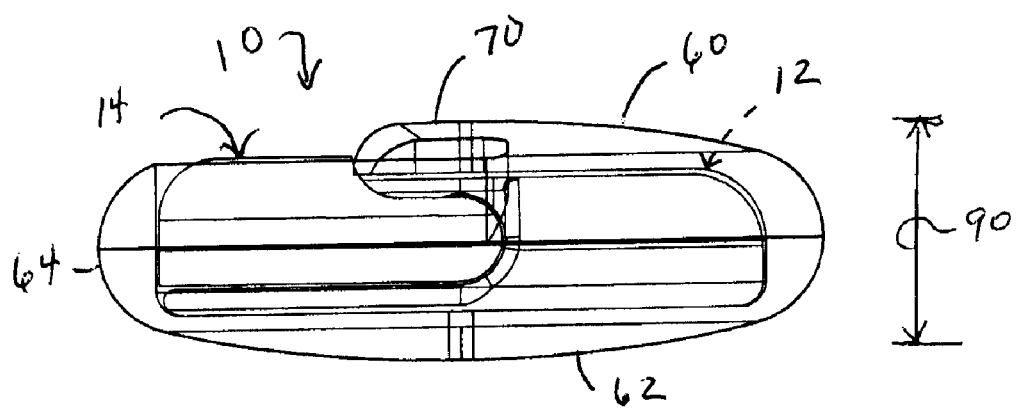
FIG. 21 is side view of the cover of FIG. 17 with the suture retention hub positioned therein.
Figure 22:
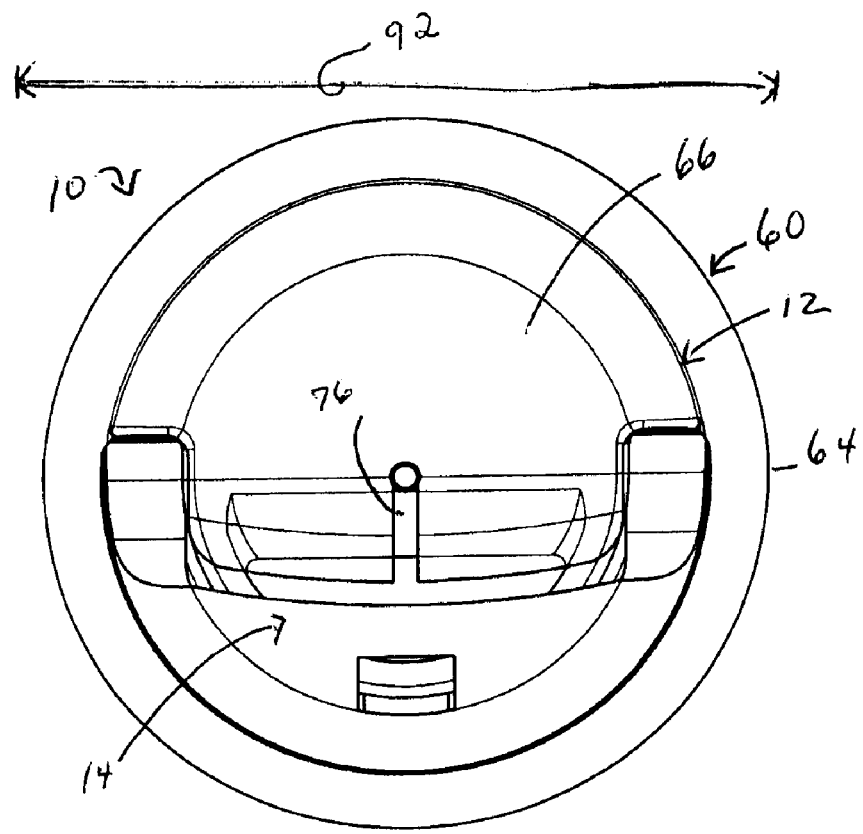
FIG. 22 is a top plan view of the cover of FIG. 17 with the suture retention hub positioned therein.

Desirably a suture 78 is positioned through the aperture 28 in the bar 24 of the first base or base 12, and through the aperture 46 of the pivot pin 38 of the second base or handle 14, as shown in FIGS. 15 and 16. The suture 78 is also positioned through the aperture 74 and the slit 76 in the cover 60 (not shown).

When it is desired to pull a portion of the suture 78 through the hub 10, as illustrated in FIG. 16, the suture 78 moves relatively easily through the hub 10 when the hub is in an un-locked position. That is, the suture 78 passes through the aperture 28 in the bar 24 and the aperture 46 in the pivot pin 38, when the second base or handle 14 is positioned at an angle, desirably at substantially a 90 degree angle, relative to the upper surface of the first base or base 12. In this position, the aperture 46 in the pivot pin 38 of the second base or handle 14 and the aperture 28 in the bar 24 of the first base or base 12 are in a substantially axial alignment. Further, the aperture 74 and slit 76 in the cover 60 are also in a substantially axial alignment.

When it is desired to hold the suture 78 in its position in the hub 10, the hub 10 may prevent movement of the suture 78 and frictionally crimp the suture in an unmovable position when the hub 10 is positioned in a locked position, as shown in FIG. 15. That is, the when the second base of handle 14 is positioned substantially parallel or planar to the upper surface 20 of the base or first base 12, the suture 78 is prevented from moving. This is due to aperture 46 in the pivot pin 38 and therefore the suture 78 therein being positioned at an angle, and desirably substantially a 90 degree angle, relative to the aperture 28 in the bar 24 in the first base or base 12 and the suture 78 positioned therein, and crimps the suture 78 against the inner surface 26 of the bar 24.

For example, when the suture 78 is to be placed in tension, the suture 78 is not movable relative to the hub 10 when the second base or handle 14 is positioned in the closed, locked position. The suture 78 greatly resists pressure to move through the hub 10 when positioned in this frictional, crimped, non-aligned position, which essentially locks the suture 78 in a non-moveable position against a device, such as a fastener, which may be positioned on the opposite end of the suture 78. That is, the hub 10 will hold the suture 78 in a position until an excess of 3 pounds of pressure is applied to the suture 78.

In a method of use, a suture retention hub 10 is provided with a suture 78 positioned therethrough. The suture 78 may be coupled to a device, for example only, a T-bar fastener device, at an opposite end (not shown). The T-bar fastener may be positioned through a patient's skin and into an organ, such as, for example only, a patient's stomach (not shown). The T-bar fastener is desirably positioned against a stomach wall (not shown). The suture 78 extends desirably from the fastener to and through the suture retention hub 10 positioned externally on the patient's skin (not shown).

The hub 10 desirably has the second base or handle 14 positioned transversely at about a 90 degree angle relative to the upper surface 20 of the first base or base 12 of the hub 10, which is desirably positioned in the cover 60. In this position, the suture 78 is substantially axially aligned through the various components of the hub 10, and the suture 78 moves freely through the aperture 28 in the bar 24 of the first base or base 12 and through the aperture 46 in the pivot pin 38 of the second base or handle 14 (FIG. 16) as well as through the aperture 74 and slit 76 in the cover 60 (not shown). This movement allows a health care provider to adjust the tension between the fastener 80 and the hub 10 via the suture 78. Once sufficient tension has been applied and the hub 10 is desirably positioned against the patient's skin 82, the position of the suture 78 in the hub 10 is locked via the latch assembly of the hub 10. This locked position crimps the suture 78 and prohibits movement of the suture 78 within the hub 10, so that the tension will remain constant. That is, the second base or handle 14 is moved or pivoted so that it is substantially parallel or planar to the upper surface 20 of the base or first base 12 (FIG. 15).

To mechanically lock the hub into this position, the second base or handle 14 is pivoted to rest against the flange 36 at the edge 35 of the first base or base 12, and the latch assembly, the knob 58 on the inner edge 56 of the second base or handle 14 is positioned through the opening 37 in the flange 36, thereby positioning the second base or handle 14 in the locked position. In this position, as previously described herein, the suture 78 in the aperture 46 of the pivot pin 38 of the second base or handle 14 is rotated at about a 90 degree angle away from its previous substantially axial alignment with a portion of the suture 78 in the aperture 28 in the bar 24 of the first base 12. This rotation also serves to frictionally crimp or hold the suture 78 between an outer surface 88 of the pivot pin 38 and the inner surface 26 of the bar 24.

The suture 78 may then be knotted on the upper surface 66 of the cover 60, if desired (not shown). In the locked position, the suture 78 in the hub 10 is positioned in a circuitous, crimped "Z" or "S" configuration.

While it is possible to un-latch the second base or handle 14 from its locked position on the first base or base 12, in many procedures, it would be undesirable to do so. The lip 50 of the upper surface 48 of the second base or handle 14 may be moved upward, thereby moving the knob 58 out of the opening 37 in the flange 36 thereby un-locking the suture 78 in the hub 10. Such a procedure may relieve tension on the suture 78, depending upon the angle upon which the second base or handle 14 is positioned.

The first base or base 12 of the hub 10 is desirably constructed from a medical grade polycarbonate. The second base or handle 14 of the hub 10 is desirably constructed from a medical grade polypropylene. The cover 60 of the hub 10 is desirably constructed from a medical grade silicone. It will be appreciated, however, that any component of the hub 10 may be constructed from any medically acceptable material(s), so long as the hub 10 operate as shown and/or described herein.

Moreover, the configuration of the hub 10 and/or any component(s) thereof is intended as non-limiting. That is, neither the hub 10 or any component thereof is intended to be limited to a single configuration. Any configuration(s) of any component(s) which permit the hub 10 to operate as shown and/or described herein may be used.

It is desirable that the hub 10 provide a low, flat profile, to increase comfort and decrease the chance of inadvertently hooking the hub 10 on clothing, other devices, and so forth. The height dimension 90 of the hub 10 is desirably in a range of about 0.08 to about 0.140 inches. Even more desirably, the height dimension of the hub 10 is in a range of about 0.09 to about 0.13 inches. Most desirably, the height dimension of the hub 10 is in a range of about 0.100 to about 0.120 inches. When the hub 10 is positioned in the cover, the height dimension is desirably in a range of about 0.150 to about 0.250 inches. Even more desirably, the height dimension of the hub 10 in the cover is about 0.175 to about 0.225 inches. Most desirably, the height dimension of the hub 10 in the cover 60 is about 0.190 to about 0.210 inches.

The hub 10 is desirably wider than its height dimension. Therefore, the hub 10 desirably has a width dimension 92, which includes the cover 60, in a range of about 0.450 to about 0.700. Even more desirably, the width dimension of the hub 10 in the cover 60 is in a range of about 0.048 to about 0.675 inches. Most desirably, the width dimension of the of the hub 10 in the cover 60 is about 0.500 to about 0.650 inches.

The diameter of the aperture 28 through the bar 24 of the first base or base 12, the diameter of the aperture 46 through the pivot pin 38 of the second base or handle 14, the diameter of the aperture 74 and the end diameter of the slit 76 in the cover 60 are each desirably in a range of about 0.024 to about 0.026 inches. More desirably, the diameter of the apertures 28, 46, 74 and end of slit 76 are about 0.025 inches.

It will be appreciated that the first base or base 12 and/or the second base or handle 14 may not include apertures therethrough for the suture (not shown). In this alternative, a suture may extend into an opening in the bar of the base, and may be crimped by the rotation of the pivot pin. In this embodiment, the pivot pin may, but not by way of limitation, contain a bump, knob, and so forth, to create a frictional resistance between the pivot pin and the inner surface of the bar (not shown). In other alternatives, only one opening only through the base 12 may be utilized (not shown). In other alternatives, only one opening through the handle 14 may be utilized (not shown).

While the present invention has been described in connection with certain preferred embodiments, it is to be understood that the subject matter encompassed by way of the present invention is not to be limited to those specific embodiments. On the contrary, it will be appreciated that some elements and/or articles may be used with other elements or articles. It is intended for the subject matter of the invention to include all alternatives, modifications and equivalents as can be included within the spirit and scope of the invention.

What is claimed is:

1. A suture retention hub comprising:
    a base including a bar, the bar has an opening formed therethrough configured to moveably hold a portion of a handle within at least a portion of the base, the base formed to include an aperture therethrough; and
    a handle configured to moveably fit within at least a portion of the base, a portion of the handle having an aperture formed therethough, the portion of the handle positioned within the portion of the base to permit movement of the handle;
    wherein the aperture in the base and the aperture in the handle are substantially in an axial alignment when the handle is positioned transversely relative to an upper surface of the base such that a suture positioned therethrough moves readily through the apertures, and
    wherein the aperture in the base and the aperture in the handle are substantially out of an axial alignment when an upper surface of the handle is positioned in a parallel alignment relative to the upper surface of the base such that a suture positioned therethrough is frictionally crimped in its position in the handle and the base, thereby preventing movement of the suture within the hub.

2. The suture retention hub of claim 1, wherein the portion of the handle is a pivot pin.

3. The suture retention hub of claim 2, wherein the handle is formed from a resilient material, and the handle resiliently bends to pivotably couple to the base of the hub.

4. A suture retention hub comprising:
    a base configured to moveably hold a handle within at least a portion of the base, the base formed to include an aperture therethrough;
    a handle configured to moveably fit within at least a portion of the base, a portion of the handle having an aperture formed therethough, the portion of the handle positioned within the portion of the base to permit movement of the handle; and
    a cover, and the cover extends at least over the lower surface of the hub,
    wherein the aperture in the base and the aperture in the handle are substantially in an axial alignment when the handle is positioned transversely relative to an upper surface of the base such that a suture positioned therethrough moves readily through the apertures, and
    wherein the aperture in the base and the aperture in the handle are substantially out of an axial alignment when an upper surface of the handle is positioned in a parallel alignment relative to the upper surface of the base such that a suture positioned therethrough is frictionally crimped in its position in the handle and the base, thereby preventing movement of the suture within the hub.

5. The suture retention hub of claim 1, wherein the width dimension of the hub is greater than the height dimension of the hub.

6. The suture retention hub of claim 1, wherein the suture follows a circuitous path through the hub when the handle is positioned out of alignment with the aperture in the base, which causes frictional resistance of the suture within the hub.

7. The suture retention hub of claim 1, wherein the suture follows a substantially straight path through the hub when the handle is positioned in alignment with the aperture in the base, which substantially removes frictional resistance to the suture within the hub.

8. The suture retention hub of claim 1, wherein when the aperture in the base and the aperture in the handle are in an axial alignment when the handle is positioned transversely relative to an upper surface of the base such that a suture positioned therethrough moves readily through the apertures in the hub, the hub is in an un-locked position.

9. The suture retention hub of claim 1, wherein when the aperture in the base and the aperture in the handle are out of an axial alignment when an upper surface of the handle is positioned in a parallel alignment relative to the upper surface of the base such that a suture positioned therethrough is frictionally crimped in its position in the handle and the base, thereby preventing movement of the suture within the hub, the hub is in a locked position.

10. A suture retention hub comprising:
a base configured to moveably hold a handle within at least a portion of the base, the base formed to include an aperture therethrough;
a handle configured to moveably fit within at least a portion of the base, a portion of the handle having an aperture formed therethough, the portion of the handle positioned within the portion of the base to permit movement of the handle; and
a latch assembly comprising a knob provided by the handle which extends through a cooperative opening formed in the base to lock the handle in a position relative to the base,
wherein the aperture in the base and the aperture in the handle are substantially in an axial alignment when the knob is positioned not to extend through the opening in the base and the handle is moved at least 35 degrees away from the base, such that the hub is positioned in an un-locked position and the hub permits movement of the suture through the hub, and wherein the aperture in the base and the aperture in the handle are substantially out of an axial alignment when the latch assembly is in a locked position such that a suture positioned therethrough is frictionally crimped in its position in the handle and the base, thereby preventing movement of the suture through the hub.

11. A suture retention hub comprising:
a first base including an upper surface; and
a second base moveably coupled to the first base, at least one of the first base and the second base formed to include at least one aperture therethough;
wherein when the second base is positioned substantially at a 90 degree angle relative to the upper surface of the first base, a suture positioned through the aperture is moveable through the hub, and
wherein when the second base is positioned substantially parallel to the upper surface of the first base, a suture positioned through the aperture is not moveable through the hub.

12. The suture retention hub of claim 11, wherein the first base includes a bar, and the bar has an opening formed therethrough configured to moveably hold the portion of the second base.

13. The suture retention hub of claim 12, wherein the second base comprises a handle.

14. The suture retention hub of claim 13, wherein the portion of the handle is a pivot pin.

15. The suture retention hub of claim 14, wherein handle is formed from a resilient material, and the handle resiliently bends to pivotably couple to the base of the hub.

16. The suture retention hub of claim 11, wherein the hub includes a cover, and the cover extends at least over the lower surface of the hub.

17. The suture retention hub of claim 4, wherein the width dimension of the hub is greater than the height dimension of the hub.

18. The suture retention hub of claim 4, wherein when the aperture in the base and the aperture in the handle are in an axial alignment when the handle is positioned transversely relative to an upper surface of the base such that a suture positioned therethrough moves readily through the apertures in the hub, the hub is in an un-locked position.

19. The suture retention hub of claim 4, wherein when the aperture in the base and the aperture in the handle are out of an axial alignment when an upper surface of the handle is positioned in a parallel alignment relative to the upper surface of the base such that a suture positioned therethrough is frictionally crimped in its position in the handle and the base, thereby preventing movement of the suture within the hub, the hub is in a locked position.

* * * * *